United States Patent [19]
Tosa

[11] Patent Number: 5,869,261
[45] Date of Patent: Feb. 9, 1999

[54] OPTICAL IMMUNITY MEASUREMENT METHOD AND APPARATUS THEREFOR

[75] Inventor: Kaori Tosa, Kusatsu, Japan

[73] Assignee: Daikin Industries, Ltd., Osaka, Japan

[21] Appl. No.: 428,136

[22] PCT Filed: Aug. 30, 1994

[86] PCT No.: PCT/JP94/01430

§ 371 Date: Aug. 30, 1995

§ 102(e) Date: Aug. 30, 1995

[87] PCT Pub. No.: WO95/06876

PCT Pub. Date: Mar. 9, 1995

[30] Foreign Application Priority Data

Aug. 31, 1993 [JP] Japan ................................. 5-215965

[51] Int. Cl.[6] .................................................. G01N 33/53
[52] U.S. Cl. ..................... 435/7.1; 436/517; 436/518; 436/501; 436/165; 436/805; 436/543; 436/547; 436/172
[58] Field of Search ........................... 435/7.1; 436/517, 436/518, 501, 805, 543, 547, 165, 172

[56] References Cited

U.S. PATENT DOCUMENTS 4,476,230  10/1984  Sieber ........................................ 436/517
4,810,658   3/1989  Shanks et al. ............................. 436/172
4,857,454   8/1989  Freundlich et al. ....................... 435/7.4
5,469,264  11/1995  Shigemori .................................. 356/417

FOREIGN PATENT DOCUMENTS

WO89/09408  10/1989  WIPO.
WO93/25908  12/1993  WIPO.

OTHER PUBLICATIONS

Atkins, "Physical Chemistry" (Third Edition) Oxford University Press, USA (1986) pp. 698–708.

Primary Examiner—Paula K. Hutzell
Assistant Examiner—Heather A. Bakalyar
Attorney, Agent, or Firm—Beveridge, DeGrandi, Weilacher & Young, LLP

[57] ABSTRACT

When measurement by a 1 step sandwich method is performed, a signal corresponding to a quantity of labeled antibodies A is sampled, the labeled antibodies being constrained in the vicinity of a surface of an optical waveguide (D) by an antigen-antibody reaction. A differential value by time at the beginning of the measurement and a signal corresponding to an extent of an immunological reaction at a time at which the signal becomes nearly stable are obtained based upon the sampled signals. The extent of the immunological reaction is then uniquely determined based upon the differential value by time and the signal corresponding to the extent of the immunological reaction.

16 Claims, 4 Drawing Sheets

OPTICAL IMMUNITY MEASUREMENT METHOD AND APPARATUS THEREFOR

TECHNICAL FIELD

The present invention relates to an optical immunity measurement method and apparatus therefor. More particularly, the present invention relates to a method and apparatus for measuring an extent of immunological reaction based upon an optical signal corresponding to a quantity of a labeled substance which is constrained in the vicinity of a surface of an optical waveguide by an antigen-antibody reaction. The antigen-antibody reaction is performed by fixing antigens or antibodies on the surface of the optical waveguide and by contacting a liquid with the fixed antigens or the antibodies which liquid is obtained by previously mixing a liquid which includes antigens or antibodies labeled with a target substance for measurement so as to perform antigen-antibody reaction.

BACKGROUND ART

In the past, a method for measuring an extent of immunological reaction based upon an intensity of excited fluorescent light is proposed. The excited fluorescent light is obtained by previously fixing antigens or antibodies on a surface of a slab-type optical waveguide, by performing antigen-antibody reaction between antibodies or antigens in a test liquid for measurement and the fixed antigens or antibodies, by performing antigen-antibody reaction between labeled antigens or labeled antibodies labeled with fluorescence dye and the reacted antibodies or antigens, by introducing an exciting light into the slab-type optical waveguide which light propagates in the slab-type optical waveguide in a total reflection manner, so as to generate an evanescent wave component, and by exciting fluorescent dye by the generated evanescent wave component the dye being constrained in the vicinity of the surface of the slab-type optical waveguide. In this case, a so-called end-point method is generally employed which detects an intensity of the fluorescent light when an intensity of the fluorescent light becomes nearly stable and calculates an extent of immunological reaction based upon the detected intensity. Also, a measurement signal obtained by the method is referred to as an end-point signal.

Further, when a measurement is performed by employing the above method, a method is proposed which shortens a required time for measurement by previously performing the antigen-antibody reaction by mixing a test liquid for measurement and labeled antigens or labeled antibodies, i.e., by mixing the test liquid with the labeled antigens prior to performing the immunological measurement (hereinafter, this method is referred to as a 1 step sandwich method).

When an immunity measurement is performed using the former method, antigen-antibody reaction should be performed between the antigens or antibodies fixed on the surface of the slab-type optical waveguide and the antibodies or antigens included in the test liquid for measurement. The liquid for measurement should then be discharged, and the antigen-antibody reaction should be performed between the labeled antigens or labeled antibodies and the reacted antibodies or antigens. Therefore, time for performing the antigen-antibody reaction twice is needed and a time for discharging the test liquid is needed, so that a required measurement time in its entirety is lengthened. Further, when the test liquid is discharged, the test liquid should be discharged up to nearly 100% so that the liquid which includes labeled antigens or labeled antibodies is not diluted by remaining test liquid. When a vessel for housing the test liquid is small in size, a disadvantage arises in that the discharging operation becomes difficult. Of course, when the test liquid is imperfectly discharged, a concentration of the labeled antigens or labeled antibodies is diluted so that a quantity of antigens or antibodies which are constrained in the vicinity of the surface of the optical waveguide by the antigen-antibody reaction is lessened. Therefore, the accuracy of immunological measurement is lowered.

When an immunological measurement is performed using the latter method (1 step sandwich method), an operation for discharging the test liquid is not needed at all, and a required time for an immunological measurement is remarkably shortened by performing the antigen-antibody reaction in parallel to another processing, such as, for example, an immunological measurement processing based upon another test liquid for measurement, because the labeled antigens or labeled antibodies and the test liquid are previously mixed so that the antigen-antibody reaction is previously performed. Of course, a lower accuracy of the immunological measurement due to imperfect discharge of the test liquid is not realized at all.

A disadvantage arises in that the same intensity of fluorescent light is possibly detected when a concentration of antigens or antibodies in a test liquid is high and when a concentration of antigens or antibodies in a test liquid for measurement is low. The disadvantage cannot be ignored because a mistaken measurement result badly affects a human body by taking a condition into consideration which condition that measurement of an extent of immunological reaction is mostly performed on contradiction that medical treatment and the like is performed thereafter.

Occurrence of the above disadvantage is further described in detail.

In the 1 step sandwich method, an antigen-antibody reaction is performed between antigens in a test liquid for measurement and labeled antibodies, by previously mixing a reagent solution which includes labeled antibodies and the test liquid, for example. The labeled antibodies are obtained by labeling antibodies with fluorescent dye. A concentration of antigens in the test liquid is unknown. The mixed liquid is under a condition that the labeled antibodies excessively exist, or the antigens excessively exist, or the labeled antibodies and antigens exist in a nearly balanced condition, depending upon the concentration of the antigens. When the labeled antibodies excessively exist, many of the labeled antibodies exist in the mixed liquid which are not included in the antigen-antibody reaction. When the antigens excessively exist in the mixed liquid, many of the antigens exist in the mixed liquid which are not included in the antigen-antibody reaction. When the labeled antibodies and antigens exist in a nearly balanced condition, the labeled antibodies and the antigens scarcely exist in the mixed liquid which antibodies and which antigens are not included in the antigen-antibody reaction.

The above disadvantage does not occur when the labeled antibodies excessively exist or when the labeled antibodies and antigens exist in a nearly balanced condition. However, when the antigens excessively exist in the mixed liquid, not only the antigens which have already been included in the antigen-antibody reaction with the labeled antibodies, but also the antigens which have not been included in the antigen-antibody reaction with the labeled antibodies, are included in the antigen-antibody reaction with the antibodies which are fixed on the surface of the slab-type optical waveguide. When a quantity of the latter antigen-antibody reaction increased, a quantity of the labeled antibodies which are constrained in the vicinity of the surface of the slab-type optical waveguide is lessened. Therefore, the same intensity of fluorescent light is obtained in cases where the concentration of antigens in the test liquid is low and where the concentration of antigens in the test liquid is high. Consequently, it becomes impossible to determine a concentration of antigens in a test liquid for measurement uniquely.

To resolve such a disadvantage, it is necessary that another measurement be performed based upon the 1 step sandwich method again, after the test liquid for measurement is diluted, to judge whether already obtained measurement result is correct. Specifically, when signal values of 89 and 88 arbitrary units are obtained based upon intensities of fluorescent light in cases where the test liquids for measurement is not diluted, which liquids have concentrations of $\beta$2-microglobulin of 10 $\mu$g/ml and 300 $\mu$g/ml, respectively, signal values of 11 and 131 respectively are obtained based upon intensities of fluorescent light when the test liquids for measurement are diluted by ten times. Therefore, concentrations of $\beta$2-microglobulin are uniquely determined to be 10 $\mu$g/ml and 300 $\mu$g/ml, respectively. As a result, an extent of immunological reaction is fairly accurately measured. But, new disadvantages arise in that a required time for measurement is remarkably lengthened for the measurement's entirety and that a required quantity of labeled antibodies for measurement is increased. Of course, a required number of optical waveguides on which antibodies are previously fixed also is increased. Further, a disadvantage arises in that the accuracy in measurement of a degree of the antigen-antibody reaction is lowered because a measurement error is generated due to differences between measurement timings and between optical waveguides on which the antibodies are fixed, and the like.

DISCLOSURE OF THE INVENTION

The present invention was made in view of the above problems.

It is an object of the present invention to offer an optical immunological measurement method and apparatus therefor which uniquely determines an extent of immunological reaction when the same measurement signals are obtained despite different extent of immunological reaction relative to one another.

To perform the above object, an optical immunological measurement method according to a first embodiment of the invention is a method for measuring an extent of immunological reaction based upon an optical signal corresponding to a quantity of a labeled substance which is constrained in the vicinity of a surface of an optical waveguide by an antigen-antibody reaction. The antigen-antibody reaction is performed by fixing antigens or antibodies on the surface of the optical waveguide and by contacting a liquid with the fixed antigens or the antibodies, which liquid is obtained by previously mixing a liquid which includes antigens or antibodies labeled with the labeled substance, and a test liquid which includes the target substance for measurement so as to perform a antigen-antibody reaction. The method comprises the steps of;

obtaining a differential value by time of a signal which is obtained after the liquid, which is obtained by previously carrying out an antigen-antibody reaction, contacts the fixed antigens or antibodies, obtaining a signal corresponding to the degree of immunity reaction at a time when the signal becomes nearly stable and when the differential value has already been obtained, and calculating the extent of immunological reaction based upon the differential value and the signal corresponding to the extent of immunological reaction.

This method obtains the differential value by time of the signal which is obtained after the liquid, which is obtained by previously carrying out the antigen-antibody reaction, contacts the fixed antigens or antibodies, and obtains the signal corresponding to the extent of immunological reaction at the time when the signal becomes nearly stable and when the differential value has already been obtained. This method then calculates the extent of immunological reaction based upon the differential value and the signal corresponding to the extent of immunological reaction, when the extent of immunological reaction is measured based upon the optical signal corresponding to the quantity of labeled substance which is constrained in the vicinity of the surface of the optical waveguide by antigen-antibody reaction. The antigen antibody reaction is performed by fixing antigens or antibodies on the surface of the optical waveguide and by contacting the liquid with the fixed antigens or the antibodies. The liquid is obtained by previously mixing a liquid which includes antigens or antibodies labeled with the labeled substance, and the test liquid which includes the target substance for measurement so as to perform an antigen-antibody reaction. With this method, the extent of immunological reaction is uniquely determined even when the signal has a value which corresponds to extent of immunological reactions which are different from one another.

An optical immunological measurement apparatus according to another embodiment of the invention is an apparatus for measuring an extent of immunological reaction based upon an optical signal corresponding to a quantity of a labeled substance which is constrained in the vicinity of a surface of an optical waveguide by an antigen-antibody reaction. The antigen-antibody reaction is performed by fixing antigens or antibodies on the surface of the optical waveguide and by contacting a liquid with the fixed antigens or the antibodies. The liquid is obtained by previously mixing a liquid which includes antigens or antibodies labeled with a labeled substance, and a test liquid which includes the target substance for measurement so as to perform an antigen-antibody reaction. The apparatus comprises;

differential means for obtaining a differential value by time of a signal which is obtained after the liquid which is obtained by previously carrying out an antigen-antibody reaction, contacts the fixed antigens or antibodies, saturated signal detection means for obtaining a signal corresponding to the extent of immunological reaction at a time when the signal becomes nearly stable, and immunological reaction extent calculation means for calculating the extent of immunological reaction based upon the differential value and the signal corresponding to the extent of immunological reaction.

This apparatus obtains the differential value by time of the signal by the differential means, which signal is obtained after contacting the liquid which is obtained by previously carrying out the antigen-antibody reaction with the fixed antigens or antibodies. The apparatus obtains the signal corresponding to the extent of immunological reaction by the saturated signal detection means at the time when the signal becomes nearly stable and when the differential value has already obtained, and calculates the extent of immunological reaction with the immunological reaction calculation means based upon the differential value and the signal corresponding to the extent of immunological reaction, when the degree of immunity reaction is measured based upon the optical signal corresponding to the quantity of labeled substance which is constrained in the vicinity of the surface of the optical waveguide by an antigen-antibody reaction. The antigen-antibody reaction is performed by fixing antigens or antibodies on the surface of the optical waveguide and by contacting the liquid with the fixed antigens or the antibodies (which liquid is obtained by previously mixing the liquid which includes antigens or antibodies labeled with labeled substance) and the test liquid which includes the target substance for measurement so as to perform an antigen antibody reaction. Therefore, the extent of immunological reaction is uniquely determined even when the signal has a value corresponding to extent of immunological reaction which are different from one another.

Description is made in more detail.

When liquid, which is obtained by previously carrying out an antigen-antibody reaction contacts the fixed antigens or antibodies (hereinafter, simply referred to as the fixed antibodies), and when the concentration of the antibodies or the concentration of the antigens in the test liquid is high, the quantity of non-reacted antibodies or non-reacted antigens (antibodies or antigens which are not included in the antigen-antibody reaction between the labeled antigens or labeled antibodies, and hereinafter, referred to as the non-reacted antigens) which are included in a carried out antigen-antibody reaction with the fixed antibodies becomes geat. Therefore, the quantity of the antigens which carries out the antigen-antibody reaction with the fixed antibodies, corresponds to the concentration of the antigens in the test liquid for measurement. But, a quantity of reacted antibodies or antigens (antibodies or antigens which have already been included in the antigen-antibody reaction between the labeled antigens or labeled antibodies, and hereinafter, referred to as reacted antigens) is not in proportion to the concentration of the antigens in the test liquid for measurement, because antigen-antibody reaction is carried out between the non-reacted antigens and the fixed antibodies. That is, intensities of fluorescent light which are the same are obtained in cases where the concentration of the antigens in the test liquid for measurement is high and where the concentration of the antigens in the test liquid for measurement is low. As a result, the concentration of the antigens in the test liquid for measurement is not determined uniquely.

The inventors of the present invention have found the followings:

At the beginning of the contacting of the liquid which is obtained by previously carrying out an antigen-antibody reaction with the fixed antibodies, the differential value by time of the signal corresponding to the intensity of fluorescent light (the increasing rate of the signal corresponding to the intensity of fluorescent light) becomes great, because a collision rate of the reacted antigens to the fixed antibodies is high when the concentration of the antigens in the test liquid is high. On the contrary, when the concentration of the antigens in the test liquid for measurement is low, the differential value by time of the signal corresponding to the intensity of fluorescent light becomes small, because the collision rate of the reacted antigens to the fixed antibodies is low. The inventors have found that the concentration of the antigens in the test liquid is determined uniquely based upon the signal corresponding to the intensity of fluorescent light and the differential value by time, and have completed the present invention.

BEST MODE FOR IMPLEMENTING THE INVENTION

Hereinafter, referring to the attached drawings, we explain the present invention in detail.

Figure 1:
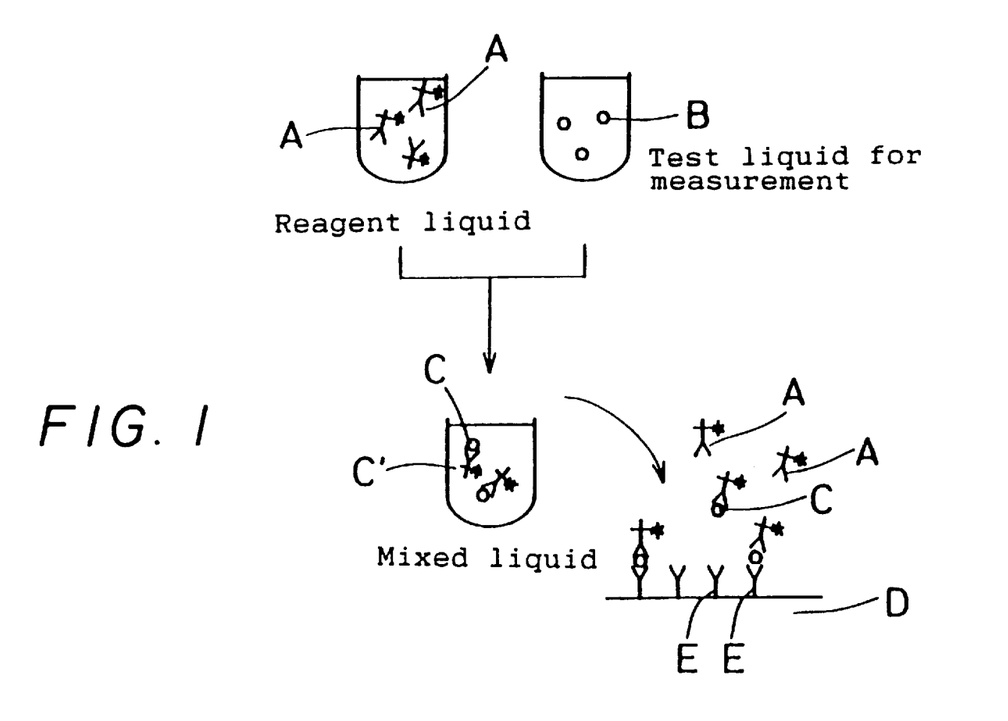
FIG. 1 is a digram which schematically explains a 1 step sandwich method.

FIG. 1 is a diagram which schematically explains a 1 step sandwich method. A reagent liquid which includes labeled antibodies A (which are made by labeling antibodies with fluorescent dye) and a test liquid for measurement are mixed prior to the measurement, so that an antigen-antibody reaction is carried out between antigens B in the test liquid and the labeled antibodies A. This mixed liquid C' in which the antigen-antibody reaction has been carried out, is contacted with antibodies E fixed on a surface of an optical waveguide D, so that an antigen-antibody reaction is carried out between reacted antigens C (which have already been reacted in an antigen-antibody reaction between the labeled antibodies A), and the antibodies E which are fixed on the surface of the optical waveguide D. Therefore, the labeled antibodies A are constrained in the vicinity of the surface of the optical waveguide.

When this method is employed, compared to a method in which the test liquid and the reagent liquid are contacted with the antibodies fixed on the surface of the optical waveguide in this order, a discharging operation of the test liquid for measurement becomes unnecessary. Also, a required time for measurement is shortened by carrying out the reaction of the labeled antibodies A and the antigens B at an arbitrary time. Further, a disadvantage is securely prevented from occurring in that a measurement accuracy is not lowered by dilution of the reagent liquid when discharging of the test liquid for measurement is imperfect.

Figure 2:
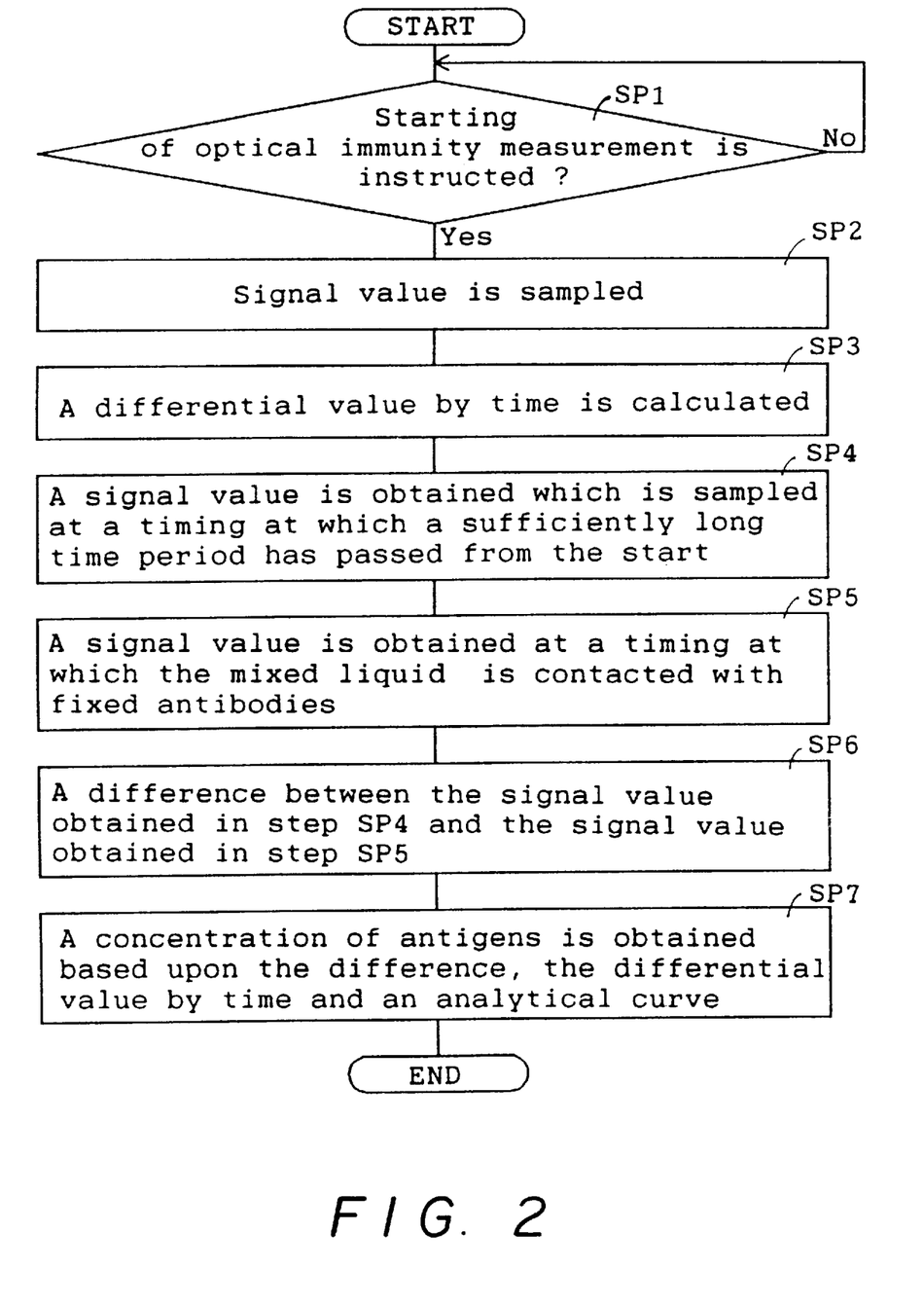
FIG. 2 is a flowchart which explains an embodiment of an optical immunological measurement method according to the present invention.

FIG. 2 is a flowchart which explains an embodiment of an optical immunological measurement method according to the present invention.

In step SP1, the start of the optical immunological measurement is postponed until it is instructed to begin. In step SP2, a signal value corresponding to a extent of immunological reaction is sampled at every predetermined time interval. The signal value is calculated by subtracting a signal value obtained at the start of the immunological reaction from a signal value obtained at the sampling time. In step SP3, a differential value by time (hereinafter, referred to as a rate signal) is calculated based upon the sampled signal values. In step SP4, a signal value is obtained which is sampled at a time at which a sufficiently long time period has passed from the starting of the process. The sufficiently long time period is meant hereinafter that a long time period until the signal value is nearly saturated. In step SP5, a signal value is obtained at a time at which the mixed liquid is contacted with antibodies fixed on the surface of the optical waveguide. In step SP6, a difference between the signal value obtained in step SP4 and the signal value obtained in step SP5 (hereinafter, referred to as an end-point signal) is calculated. Then, in step SP7, a concentration of antigens in the test liquid is obtained based upon the calculated difference, the differential value by time and an analytical curve which is previously obtained.

Figure 3:
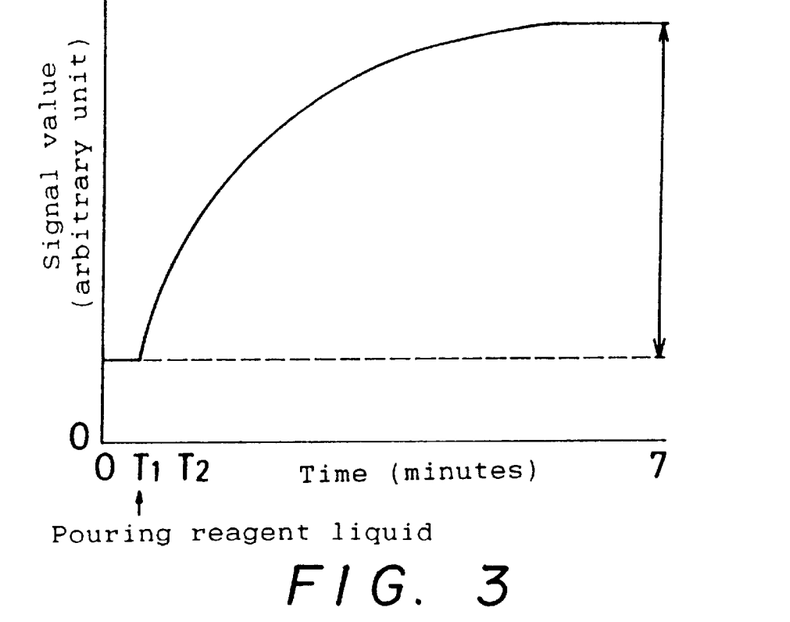
FIG. 3 is a graph illustrating the variation signal following the passage of time, which signal is obtained by the optical immunological measurement.

The processing in step SP3 may be a processing which calculates the differential value by time based upon the signal values obtained at predetermined times which are different from one another. The processing in step SP3 may also be a processing which calculates the differential values by time by performing a primary recursion processing based upon a plurality of signals which are sampled at every time interval (for example, at every second) within a predetermined time extent (for example, a time extent of 50 seconds, which is regulated by passing times T1 and T2 on a graph illustrating the variation of the signal following the passage of time, which graph is illustrated in FIG. 3). The latter method is preferably employed by taking a point into consideration where the differential value by time is calculated with high accuracy.

The processing in step SP4 may be a processing which obtains the signal value at a time (for example, 7 minutes) which is sufficiently longer than the predetermined time extent for performing the processing in step SP3. The processing in step SP4 may also be a processing which obtains the signal value at a time at which a variation rate of the signal value becomes smaller than a predetermined value. By taking a point into consideration where concentrations of antigens in plural test liquids for measurement are simultaneously measured, the former processing is preferably employed so that the processing can be simplified. In this case, it is preferable that signals are sampled within a predetermined time extent about a time at which a sufficiently long time period has passed from the starting.

The processing in step SP5 may be a processing which employs a signal which is sampled at the time when the mixed liquid contacts the antibodies fixed on the surface of the optical waveguide. The processing in step SP5 may also be a processing which calculates a signal at a starting point based upon the differential value by time obtained in step SP3, the starting point being a starting point of the predetermined time extent in step SP3 and being determined to be a time at which the mixed liquid contacts the antibodies fixed on the surface of the optical waveguide. The latter processing is preferably employed by taking an accuracy of the obtained signal into consideration.

Figure 4:
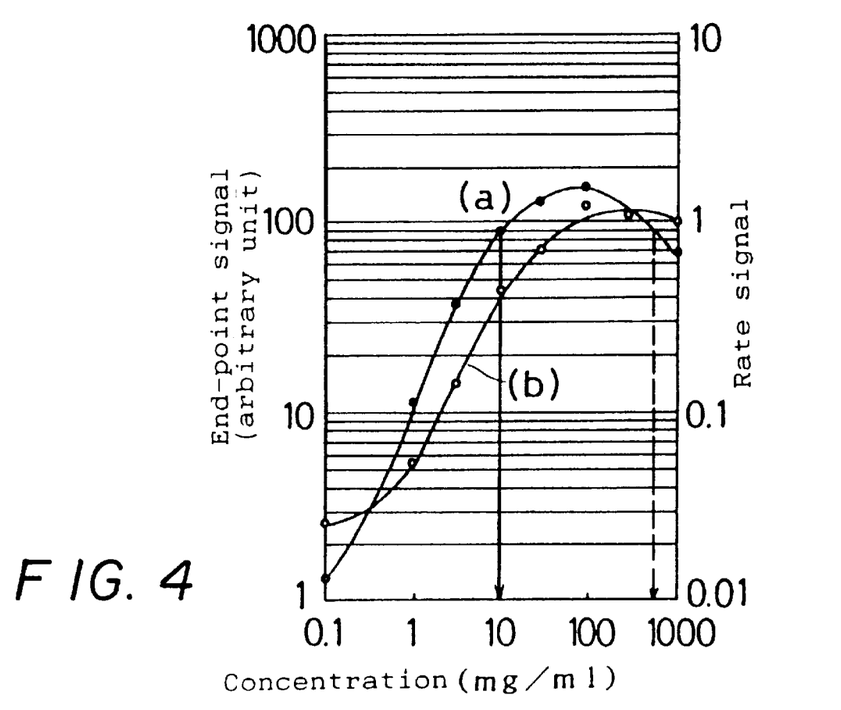
FIG. 4 is a graph illustrating analytical curves for an example of the invention.

FIG. 4 is a graph illustrating analytical curves which are an example of the invention. In FIG. 4, (a) represents an analytical curve based upon an end-point signal, while (b) represents an analytical curve based upon a rate signal. The analytical curves are intially obtained by measuring end-point signals and rate signals corresponding to standard liquids which have concentrations of antigens from one another.

As is apparent from the above description and FIG. 4, the anlytical curve based upon the end-point signal and the anlytical curve based upon the rate signal are not similar to one another. Therefore, when 2 concentrations of antigens are obtained based upon the end-point signal so that a concentration of antigens cannot be determined uniquely, a concentration of antigens can easily be determined uniquely by taking the rate signal into consideration.

Further, when the series of processings illustrated in FIG. 2 are carried out, the end-point signal and the rate signal can easily be obtained without repeating the antigen-antibody reaction based upon the 1 step sandwich method. Therefore, the required time for the measurement's entirety is securely prevented from lengthening, and the necessary quantity of the reagent liquid and the required number of optical waveguides on which antibodies are fixed, are securely prevented from increasing. Further, lowering in accuracy due to variations of measurement times and measurement environments is securely prevented from occurrence because the end-point signal and the rate signal are obtained by the measurement which is performed once.

Second Embodiment

Figure 5:
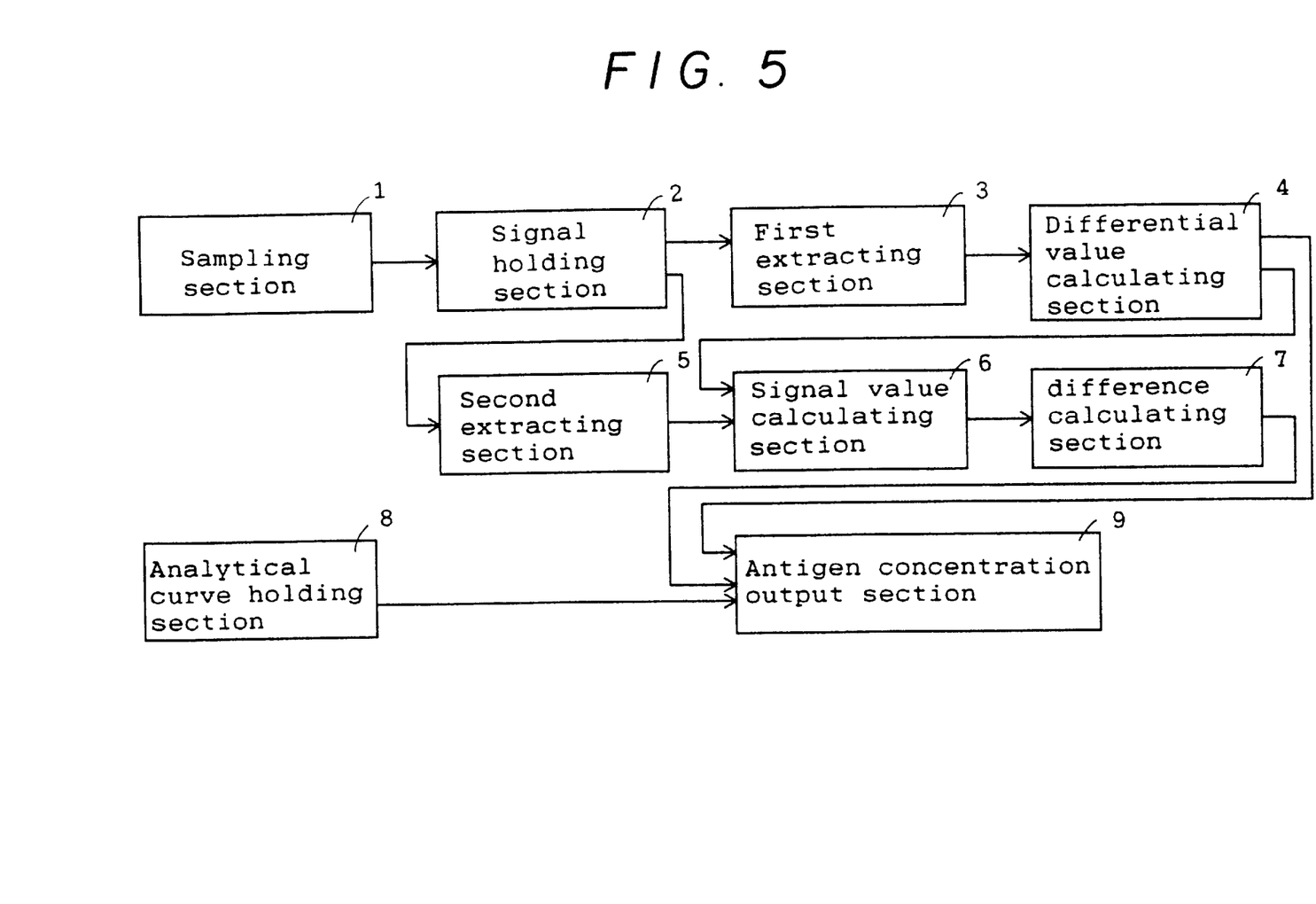
FIG. 5 is a block diagram illustrating an embodiment of an optical immunological measurement apparatus according to the present invention.

FIG. 5 is a block diagram illustrating an embodiment of an optical immunological measurement apparatus according to the present invention.

The apparatus includes a sampling section 1 for sampling a signal at every predetermined time, which signal corresponds to an intensity of fluorescent light, a signal holding section 2 for holding the sampled signals in a time sequential manner, a first extracting section 3 for extracting signals within a predetermined time extent at an initial time period from the beginning of a reaction, a differential value calculating section 4 for calculating a differential value by time based upon the signals extracted by the first extracting section 3, a second extracting section 5 for extracting a signal at a time at which a sufficiently long predetermined time has passed from the beginning of the reaction, a signal value calculating section 6 for calculating a signal value at the beginning of the reaction based upon the calculated differential value by time, a difference calculating section 7 for calculating a difference between the signal value extracted by the second extracting section 5 and the signal value calculated by the signal value calculating section 6, an analytical curve holding section 8 for holding an analytical curve based upon an end-point signal and an analytical curve based upon a rate signal, and an antigen concentration output section 9 for obtaining and outputting a concentration of antigens in a test liquid for measurement based upon the differential value by time calculated by the differential value calculating section 4, the difference calculated by the difference calculating section 7, and both analytical curves held by the analytical curve holding section 8.

Operation of each section is similar to that of the corresponding step in the above flowchart, therefore, detailed description is omitted.

Operation of the optical immunological measurement apparatus having the above arrangement is as follows.

Sampling of the signal by the sampling section 1 is started in response to an instruction to start an optical immunological measurement. A mixed liquid is contacted with antibodies based upon the 1 step sandwich method which antibodies are fixed on a surface of an optical waveguide. Therefore, the sampled signal scarcely varies in the initial stage and gradually increases after the contact of the mixed liquid with the fixed antibodies, as is illustrated in FIG. 3.

And, when the sampling of the signal for a required time extent has been carried out and the sampled signals have been held in a time sequential manner by the signal holding section 2, the signal within the predetermined time period from the beginning of the reaction is extracted by the first extracting section 3, and the differential value by time (the rate signal) is calculated by the differential value calculating section 4.

Further, the signal obtained at the time at which a sufficiently long time has passed from the starting of the reaction is extracted by the second extracting section 5. The signal value at the time at which the reaction has started, is calculated by the signal calculating section 6 based upon the rate signal which was calculated by the differential value calculating section 4. Then, the difference (the end-point signal) is calculated by the difference calculating section 7 based upon the signal which was extracted by the second extracting section 5, and the signal value which was calculated by the signal value calculating section 6.

Thereafter, the concentration of antigens is obtained and output therefrom by the antigen concentration output section 9 based upon the calculated rate signal, the calculated end-point signal and two analytical curves which are held by the analytical curve holding section 8.

For example, when end-point signals of 89 and 88 arbitrary unit respectively are obtained based upon intensities of fluorescent light in a case where test liquid for measurement are not diluted (which liquid have concentrations of β2-microglobulin of 10 μg/ml and 300 μg/ml, respectively), rate signals of 0.42 and 1.06 are obtained. Therefore, the concentrations of β2-microglobulin in the test liquids are recognized to be 10 μg/ml and 300 μg/ml respectively by referring to both analytical curves illustrated in FIG. 4.

The present invention is not limited to the above embodiments. It is possible that antigens are fixed on an optical waveguide and that a concentration of antibodies in a test liquid for measurement is measured. Various design change are applicable within an extent which would not change the scope of the present invention.

Possibility of Industrial Utilization

The present invention is preferably applied to a method and apparatus for measuring a extent of immunological reaction based upon an optical signal corresponding to a quantity of a labeled substance which is constrained in the vicinity of a surface of an optical waveguide by antigen-antibody reaction. The antigen-antibody reaction is performed by fixing antigens or antibodies on the surface of the optical waveguide and by contacting a liquid with the fixed antigens or the antibodies, which liquid is obtained by previously mixing a liquid which includes antigens or antibodies labeled with the labeled substance, and a test liquid which includes the target substance for measurement so as to perform an antigen-antibody reaction. The present invention determines the extent of immunological reaction uniquely without diluting the test liquid for measurement.

What is claimed is:

1. An optical immunological measurement method for measuring a concentration of a test substance by an immunological reaction produced according to the 1-step sandwich reaction method, the measurement being based upon an optical signal corresponding to a quantity of a labeled substance constrained to a vicinity of a surface of an optical waveguide by the immunological reaction, said measurement method comprising:

obtaining a value of the optical signal at the beginning of the immunological reaction;

obtaining a differential value by time of the optical signal after the labeled substance begins to become constrained to the vicinity of the surface of the optical waveguide;

obtaining a value of the optical signal at a time when the value of the optical signal has become nearly stable, after the differential value by time of the optical signal has already been obtained, calculating a difference between the value of the optical signal at a beginning of the immunological reaction and the value of the signal at the time when the value of the optical signal has become nearly stable, to thereby obtain an end point value, and determining the concentration of the test substance by comparing one or more calibrated concentration values corresponding to the obtained differential value by time with one or more calibrated concentration values corresponding to the obtained end point value.

2. An optical immunological measurement apparatus for measuring a concentration of a test substance by an immunological reaction produced according to the 1-step sandwich reaction method, the measurement being based upon an optical signal corresponding to a quantity of a labeled substance constrained to a vicinity of a surface of an optical waveguide by the immunological reaction, said apparatus comprising:

differential means for obtaining a differential value by time of the optical signal after the labeled substance begins to become constrained to the vicinity of the surface of the optical waveguide;

saturated signal detection means for obtaining a value of the optical signal at a time when the value of the optical signal has become nearly stable; and concentration determining means for determining the concentration of the test substance by comparing one or more calibrated concentration values corresponding to the obtained differential value by time with one or more calibrated concentration values corresponding to the value of the optical signal at the time when the value of the optical signal has become nearly stable.

3. An optical immunological measurement method according to claim 1, wherein the labeled substance includes antigens, which antigens are labeled by being bound to labeling antibodies provided with an optical marker.

4. An optical immunological measurement method according to claim 3, wherein the optical marker is a fluorescent marker.

5. An optical immunological measurement method according to claim 3, wherein anchoring antibodies are affixed to the surface of the optical waveguide, and the immunological reaction is a reaction between the antigens and the anchoring antibodies which constrains the antigens to the antibodies in the vicinity of the surface of the optical waveguide.

6. An optical immunological measurement method according to claim 1, wherein the labeled substance includes antibodies, which antibodies are labeled by being bound to labeling antigens provided with an optical marker.

7. An optical immunological measurement method according to claim 6, wherein the optical marker is a fluorescent marker.

8. An optical immunological measurement method according to claim 6, wherein anchoring antigens are affixed to the surface of the optical waveguide, and the immunological reaction is a reaction between the antibodies and the anchoring antigens which constrain the antibodies to antigens in the vicinity of the surface of the optical waveguide.

9. An optical immunological measurement method according to claim 1, wherein the differential value by time is obtained by taking differences between values of the optical signal measured at different times.

10. An optical immunological measurement method according to claim 1, wherein the differential value by time is obtained by performing a recursion process based upon a plurality of values of the optical signal measured at predetermined intervals over a predetermined time period.

11. An optical immunological measurement method according to claim 1, wherein the value of the optical signal at the beginning of the immunological reaction is obtained by measuring the value of the optical signal at the beginning of the immunological reaction.

12. An optical immunological measurement method according to claim 1, wherein the value of the optical signal at the beginning of the immunological reaction is calculated based upon the obtained differential value by time.

13. An optical immunological measurement apparatus according to claim 2, further including sampling means for sampling a value of the optical signal at predetermined time intervals.

14. An optical immunological measurement apparatus according to claim 13, wherein the differential means includes:

extracting means for extracting optical signal values sampled by the sampling means within a predetermined time period from a beginning of the immunological reaction; and differential value calculating means for calculating a differential value by time based upon the optical signal values extracted by the extracting means.

15. An optical immunological measurement apparatus according to claim 2, wherein the concentration determining means includes:

optical signal value determining means for determining a value of the optical signal at a beginning of the immunological reaction; and difference calculating means for calculating a difference between the determined value of the optical signal at the beginning of the immunological reaction and the value of the optical signal obtained by the saturated signal detection means to thereby obtain an end point value.

16. An optical immunological measurement apparatus according to claim 2, further including analytical curve holding means for holding at least one analytical curve which corresponds each of a plurality of end point values with one or more calibrated concentrations of the test substance, and at least one analytical curve which corresponds each of a plurality of differential values by time with one or more calibrated concentrations of the test substance.

* * * * *